(12) United States Patent
Roos

(10) Patent No.: US 7,420,360 B1
(45) Date of Patent: Sep. 2, 2008

(54) METHOD AND APPARATUS FOR PARTICLE COUNTING AND SIZE MEASUREMENT

(76) Inventor: Ermi Roos, 7315 SW. 79th Ct., Miami, FL (US) 33143

( * ) Notice: Subject to any disclaimer, the term of this patent is extended or adjusted under 35 U.S.C. 154(b) by 91 days.

(21) Appl. No.: 11/329,829

(22) Filed: Jan. 12, 2006

(51) Int. Cl.
*G01N 27/00* (2006.01)

(52) U.S. Cl. .................................................. 324/71.4
(58) Field of Classification Search ................. 324/71.4
See application file for complete search history.

(56) References Cited

U.S. PATENT DOCUMENTS 6,566,853 B2 * 5/2003 Li et al. ..................... 324/71.4

* cited by examiner

*Primary Examiner*—Vincent Q. Nguyen
*Assistant Examiner*—Amy He
(74) *Attorney, Agent, or Firm*—Sanchelima & Assoc. P.A.

(57) ABSTRACT

An improved electrical sensing zone apparatus and method for counting and measuring size of particles suspended in a diluted electrolytic solution. The apparatus includes an aperture that is optimized with the use of double or single tapered shapes that approximate a hyperboloid of one sheet. The flow rate is selectably controlled to maintain a sufficiently low Reynolds number to avoid boundary layer separation effects that cause noise and consequently low sensitivity. By measuring statistical moments within the aperture, an approximation of the distribution of particle sizes is achieved.

4 Claims, 7 Drawing Sheets

METHOD AND APPARATUS FOR PARTICLE COUNTING AND SIZE MEASUREMENT

BACKGROUND OF THE INVENTION

1. Field of the Invention

The present invention relates to a method and apparatus for size measurement of particles.

2. Description of the Related Art

Determining the number and size of particles suspended in a liquid solution is important for many industries. Medical applications, such as blood cell counters, have evolved from Coulter's seminal invention, U.S. Pat. No. 2,656,508 issued on Oct. 20, 1953. The preferred embodiment shown in FIGS. 1 and 6 of Coulter's patent was the beginning of what are today generically referred to as "electrical sensing zone" (ESZ) devices or methods. In an ESZ device a particle is measured by passing it through an electrical current-carrying aperture in an insulating partition between two containers, holding a conductive liquid. The motion of the particle through the aperture is caused by a pressure difference across the partition produced by a vacuum or pressure source. The presence of a particle in the aperture increases the electrical resistance of the aperture by displacing the liquid of equal volume to the particle volume. The physical chemistry of particles immersed in an electrolytic solution causes all particles (even those that are electrically conducting) to behave as if they were electrical insulators. The change in resistance may be detected as an increase in voltage across the aperture, or a decrease in current through the aperture. The change in resistance is approximately proportional to the volume of the particle. It is this approximate relationship between aperture resistance change and particle volume that gives the ESZ method good accuracy compared to several other methods of particle size measurement. On the other hand, the ESZ method has comparatively low sensitivity to submicrometer particles due to a multiplicity of noise sources in the aperture, comprising thermal noise due to aperture resistance, noise due to turbulence caused by electrical heating of the liquid in the aperture, noise due to hydrodynamic turbulence caused by flow of liquid through the aperture, noise caused by acoustic interference, noise caused by electrical interference and noise caused by mechanical vibrations. The deleterious effects of noise in the ESZ instrument are magnified by the fact that a signal pulse created by the passing of a particle through the aperture must exceed a predetermined threshold voltage in order to be detected. The threshold voltage must be set high enough so that the peaks of the noise will not falsely trigger the threshold circuit enough times to substantially interfere with the true pulses generated by the particles. The peak of the random noise is several times the root mean square (r.m.s.) level, and this requires the threshold voltage to be set a multiple number of times higher than the r.m.s. noise level. This causes a loss in sensitivity.

The usual aperture shape used in commercial prior art ESZ instruments is the circular cylinder. Until now, this has been considered to be the optimum aperture shape for the highest sensitivity. The circular, cylindrical, aperture shape causes pulses due to particles to have a wide variety of shapes. A pulse due to a particle passing along the axis of the aperture has a single peak. Other particle paths can have pulses with dual peaks, because at both the entrance and the exit of the aperture, the electric field intensity is higher at the edges than at the center. The variations in pulse shapes make it necessary to have a wide bandwidth pulse amplifier so that the pulses would be reproduced by the amplifier with high fidelity. The wide bandwidth increases the noise level. The thickness of the insulating partition through which the aperture is bored must be at least 30 micrometers (μm), the length-to-diameter ratio of the aperture is large, and this results in poor sensitivity. This is because the internal volume of the aperture must be small for high sensitivity, and a large thickness of the partition makes the aperture length long, which makes the aperture volume large.

The circular, cylindrical, aperture causes boundary-layer separation of the liquid therein. The boundary-layer separation produces noise due to turbulence. At the input of the aperture, there is a hydrodynamic constriction of the fluid flow diameter. At the output of the aperture, there is a jet oriented along the axis that is surrounded by backflow of toroidal shape. Some of the particles that have passed through the aperture are captured by the backflow and recirculate near the exit of the aperture, and this causes noise in the form of false particle pulses.

The measurement range, or "dynamic range" of an aperture is limited to about 20/1 in particle diameter, making the ESZ instrument useful for relatively narrow particle size distributions.

Most particle size analysis done with the ESZ instrument is done with apertures 30 μm in diameter, or larger. Apertures smaller in diameter have been available commercially for prior art instruments, but these smaller apertures have been little used because of their tendency to be plugged by debris. If the aperture is plugged, the instrument cannot continue to measure particles until the plug is dislodged.

Even if debris does not cause plugging, it can cause particles to be measured that are not part of the sample being tested. To keep debris from interfering with the sample, the sample concentration must be significantly higher than the debris concentration. But the sample concentration must be low enough to avoid multiple sample particles from being simultaneously in the aperture. This is called "coincidence." Coincidence of particles in the aperture can cause errors in the measured particle size distribution.

U.S. Pat. No. 3,742,348 issued on Jun. 26, 1973 to Golibersuch, addresses the problems related to plugging by debris, coincidence, and low sensitivity to small particles, by allowing a multitude of particles to pass though the aperture simultaneously. This allows a larger diameter aperture to be used than is needed to detect single particles, thus reducing the frequency of plugging. Also, smaller particles can be detected than by a single-particle measurement. One of the disadvantages of this invention is that the circular, cylindrical, aperture requires a large length-to-diameter ratio (on the order of 20/1) in order to get a signal that can be analyzed by the signal processor proposed by the inventor. The only information it obtains is equivalent to what I call "$\lambda_2$" in a subsequent section of this specification, for the special case where all of the particles in the sample have equal volumes. It will be apparent that $\mu_2$, by itself, is not a significant amount of information about the particle size distribution. Also, assuming all of the particles to be the same size is a very unrealistic and restrictive assumption.

Applicant believes that the closest reference corresponds to U.S. Pat. No. 4,926,114 issued to Doutre on May 15, 1990 for an apparatus for studying particles having an aperture whose cross-sectional area changes progressively along at least part of its length. Doutre's patent discloses an apparatus and method for studying particles suspended in molten metal that includes an aperture with a current path therethrough, causing the fluid to flow through the aperture and detecting resistive pulses caused by the passage of suspended particles. An aperture with a cross-section that changes progressively along its length provides additional information about particle size.

However, it differs from the present invention because it has the same sensitivity limitations of the other prior art devices since it does not keep the Reynold's number of the fluid flow within the required range to minimize or preclude boundary layer separation effects. Doutre's patent is not even concerned with these effects since it applies to molten metals. In fact, Doutre's invention is intended for use with apertures that ideally contain no more than one particle at a time. Col. 4, lines 51-53. There is not even a suggestion of using statistical moments to make inferences about the size of the particles.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an apparatus and method for accurately measuring particles in an electrolyte and determining the size distribution of the particles.

It is another object of this invention to provide such an apparatus that permits the counting and size distribution determination of particles having less than one micrometer in diameter.

It is still another object of the present invention to provide an apparatus and method for improving the signal-to-noise ratio.

Yet another object of this invention is to avoid or minimize the effects of boundary layer separation.

It is also another object of this invention to produce signals that can be analyzed by a signal processor to determine the lower-order statistical moments of the particle size distribution.

Another object of this invention is to provide an apparatus that can use larger and thus more debris resistant apertures, with substantially the same accurate results.

Another object of the invention is to extrapolate the particle size distribution obtained with an ESZ instrument below the threshold level.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

REFERENCE NUMERALS IN DRAWINGS

Figure 1:
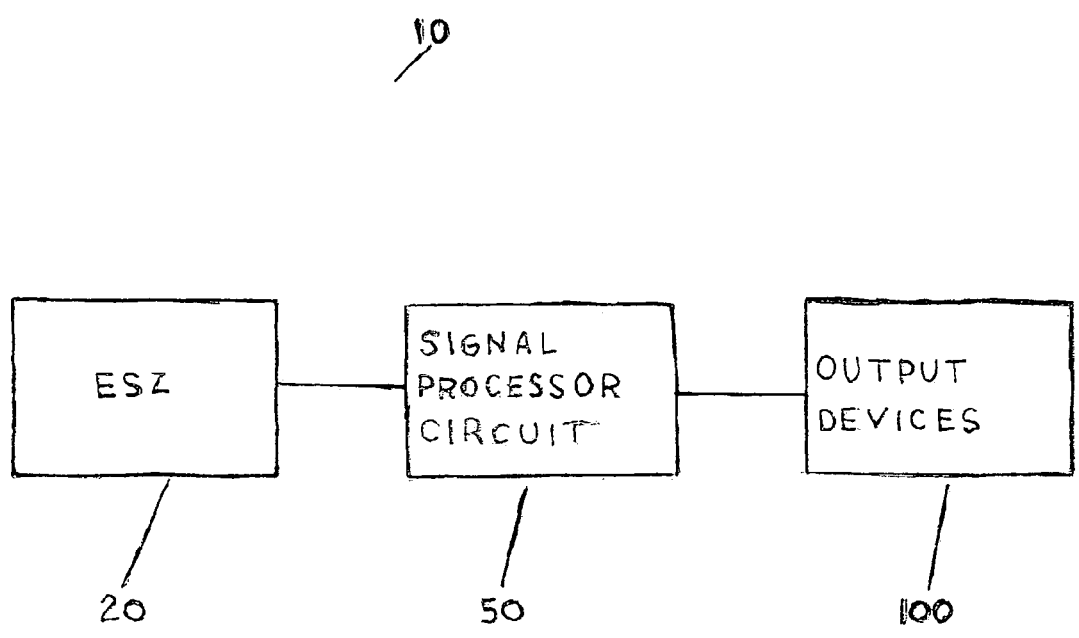
FIG. 1 is a block diagram of the method for size measurement of particles, object of the present application.

10 present invention
12 tube to vacuum or pressure source
14 vacuum or pressure means
16 liquid trap
17 inlet of aperture
18 any type of aperture
18a circular, cylindrical aperture
18b double-tapered aperture
18c single-tapered aperture
19 tapered outlet
20 ESZ assembly
21 aqueous electrolyte solution
22 particle of the sample to be measured by the instrument
23 surface-active agent (surfactant)
24 partition containing the aperture
26 low-noise aperture voltage source
27 ground connection
28 low-noise current-limiting resistor
30a electrode in nearly closed container
30b electrode in open container
32 direct current (D.C.) voltage blocking capacitor
33 D.C. coupling voltage
34 low-noise preamplifier
36 pulse amplifier
40 comparator
42 threshold voltage reference
44 pulse-height analyzer
46 particle size distribution recorder
48 output of pulse amplifier
50 signal processor
50a half-angle, $\eta$, of double-tapered aperture
50b half-angle, $\eta$, of single-tapered aperture
52a partition thickness, double-tapered aperture
52b partition thickness, single-tapered aperture
54a aperture diameter, double-tapered aperture
54b aperture diameter, single-tapered aperture
56 front surface of single-tapered aperture
58 pulse peak
60 first multiplier
62 first multiplier output
63 zeroth integrator output
64 first integrator output
65 zeroth integrator
66 first integrator
68 second integrator
70 second integrator output
72 second multiplier
74 second multiplier output
76 third integrator
78 third integrator output
80 third multiplier
82 third multiplier output
84 output processor
86 $\lambda_1$ input
88 particle size distribution estimate 90 v input
92 other inputs
100 output devices

DETAILED DESCRIPTION OF THE PREFERRED EMBODIMENT

Referring now to the drawings, where the present invention is generally referred to with numeral 10, it can be observed that it basically includes an electrical sensing zone (ESZ) assembly 20 and signal processor 50 and output devices 100, as shown in FIG. 1.

Figure 1A:
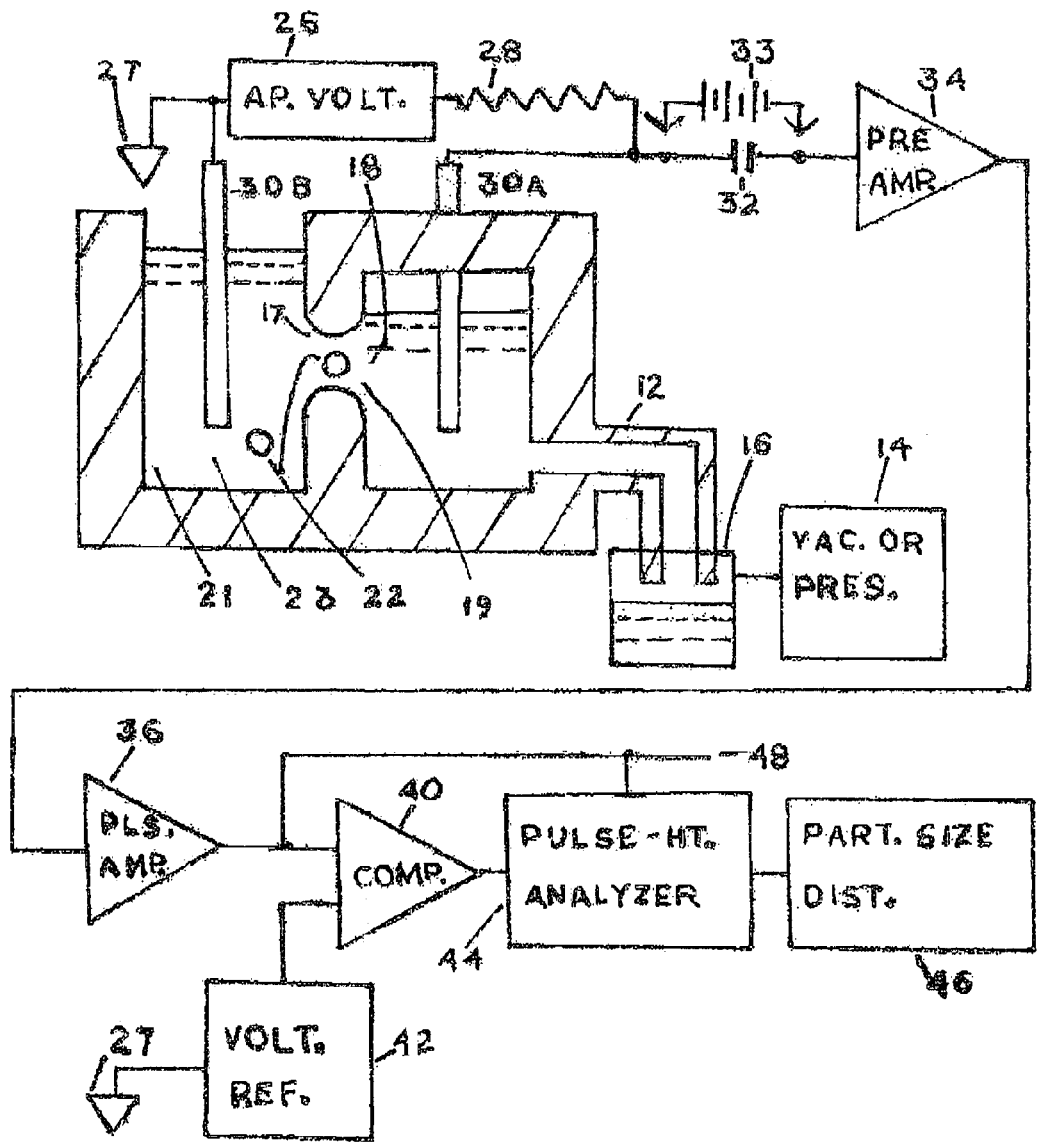
FIG. 1A is a schematic representation of one of the preferred embodiments for the improved apparatus subject of the present invention.
Figure 2:
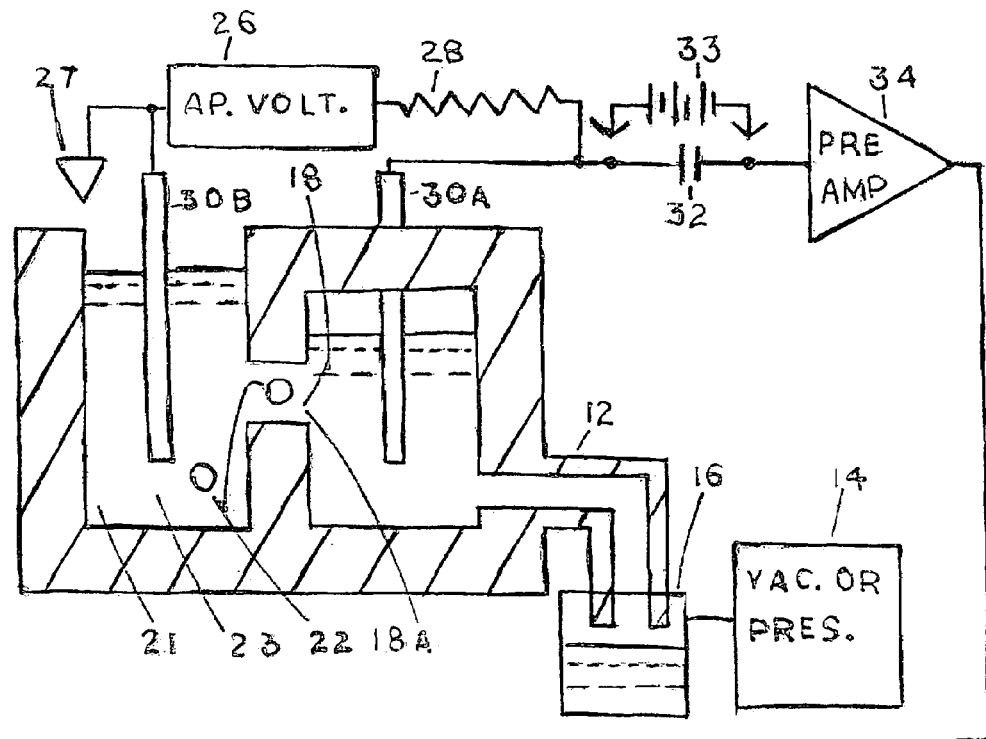
FIG. 2 is a schematic representation of a prior art electrical sensing zone (ESZ) apparatus.
Figure 2:
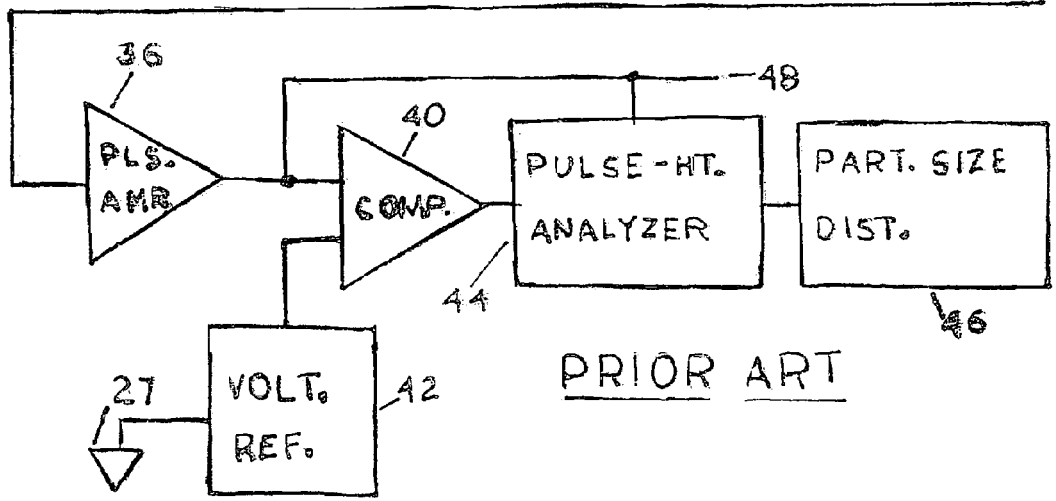
Figure 5:
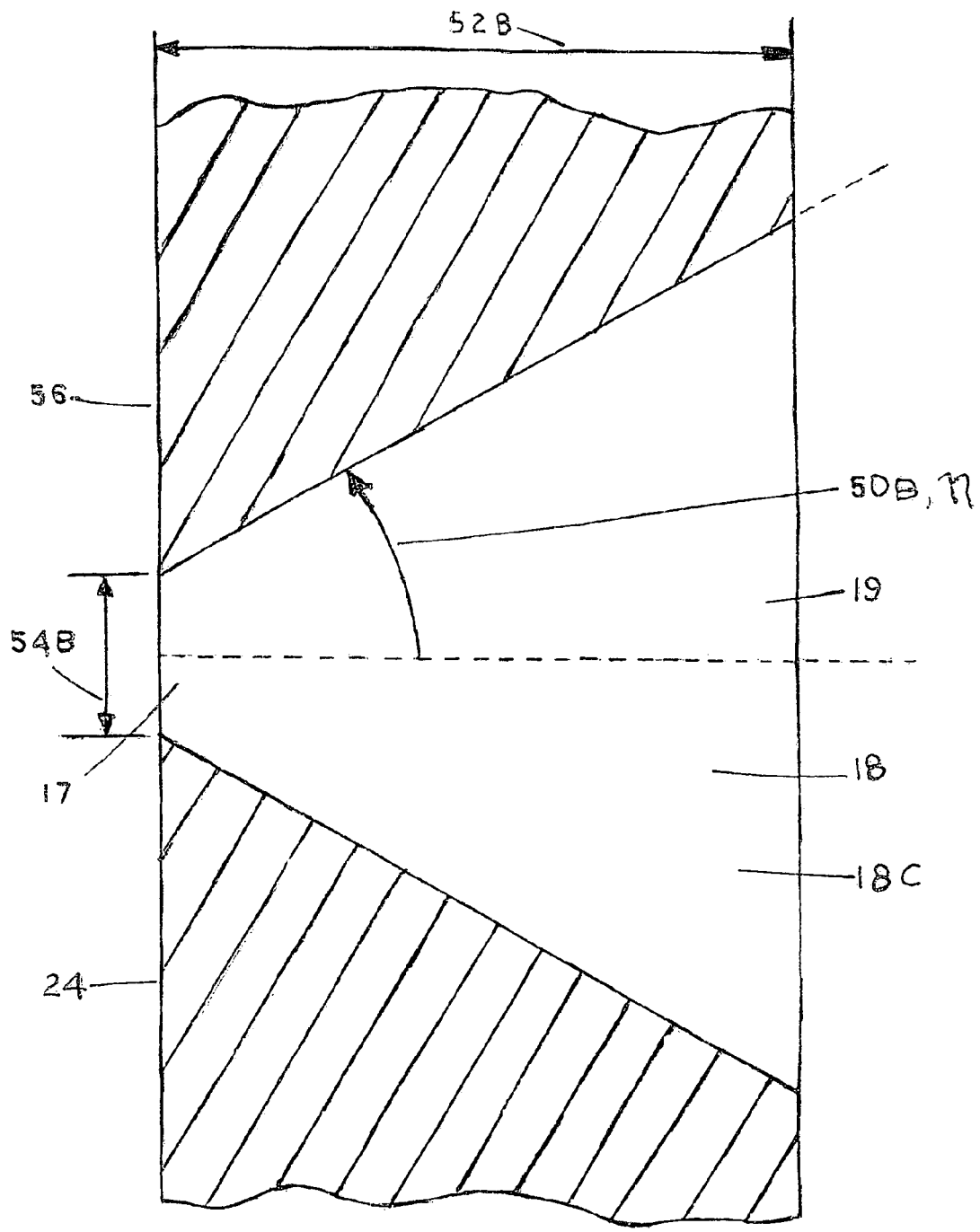
FIG. 5 is a representation of a single-tapered aperture.

ESZ assembly 20 is shown in FIG. 2 in general terms. Assembly 20 includes electrical current-carrying aperture 18 immersed in an electrolyte with controlled concentration. In FIG. 1A, ESZ assembly 20 is shown with current carrying aperture 18 with a tapered inlet 17 and outlet 19 immersed in an electrolyte with controlled concentration. As best seen in FIG. 5, in the preferred embodiment, aperture 18 has tapered outlet 19. Inlet 17 of aperture 18 has a predetermined diameter. Aperture 18 has a length of at least 30 micrometers and it is immersed in an electrolyte solution 21 with particle 22 of at least one size. Solution 21 passes through aperture 18. Vacuum or pressure means 14 causes solution 21 to pass through aperture 18 at selectable liquid flow rate with sufficiently low Reynolds number to preclude boundary layer separation effects inside and adjacent to aperture 18.

Figure 4:
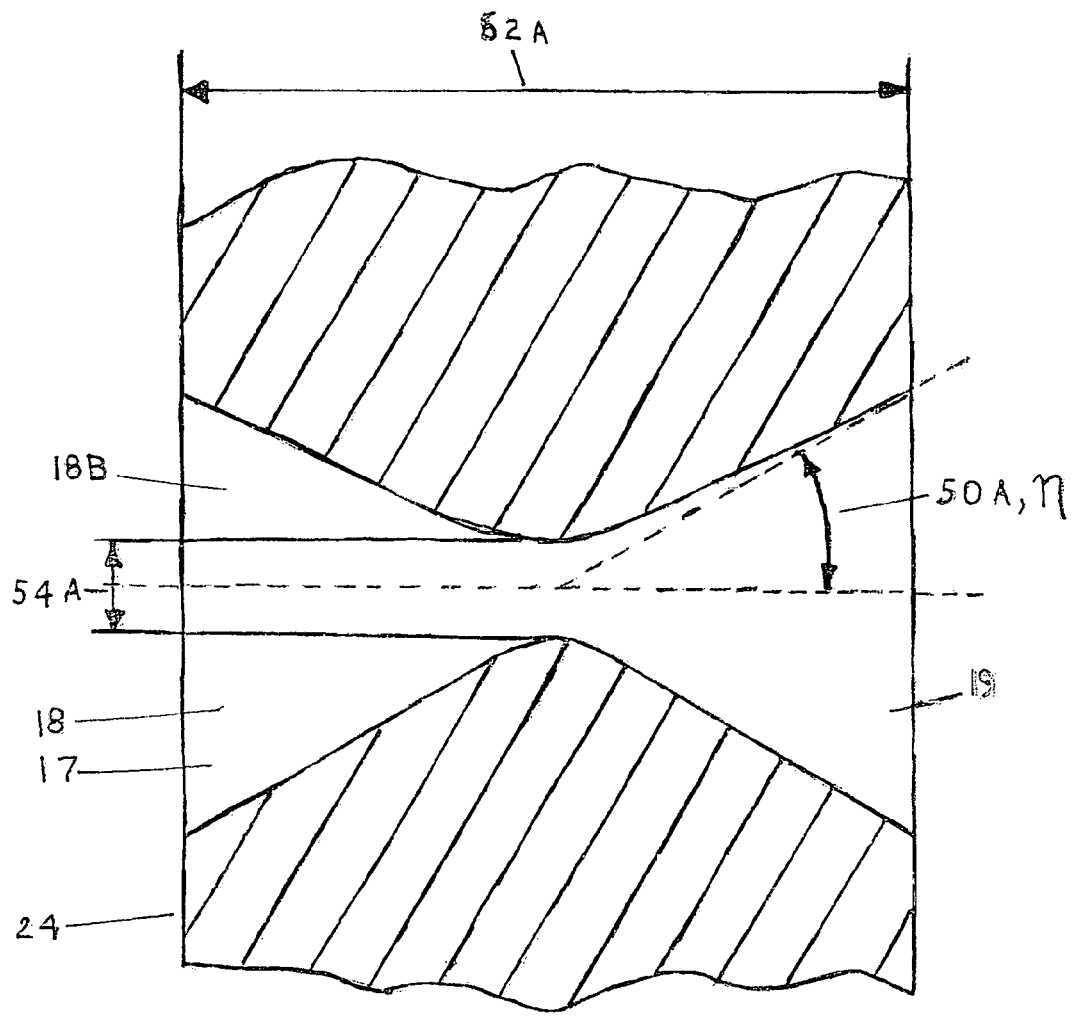
FIG. 4 is a representation of a double-tapered aperture.

In the embodiment represented in FIG. 4, aperture 18 has the double-tapered shape, which approximates a hyperboloid of one sheet. The maximum sensitivity that the invention has achieved is obtained if the angle $\eta=60$ degrees. It has been found that this shape minimizes noise and permits a more accurate measurement of the particle population and size distribution contained in the electrolyte The single-tapered aperture 18c of FIG. 5 performs similarly to the double-tapered aperture of FIG. 4, but it is easier to fabricate, and has less maximum sensitivity than the double-tapered aperture 18b. The pulses are uniformly-shaped, as in FIG. 2a. The partition thickness of the single-tapered aperture 52b can be very large.

It is well known that, if Reynolds number is low, the tendency of producing boundary layer separation at the output of the aperture 18 is reduced. Using the Navier-Stokes equations, I found the maximum value of $\eta$ that causes boundary layer separation for certain Reynolds numbers. For a Reynolds number ($R_N$) of 1, maximum $\eta$ is 74.5 degrees. For $R_N$ of 10, maximum $\eta$ is 45.8 degrees. In commercial prior art ESZ instruments, $R_N$ is in the vicinity of 500. For this $R_N$, maximum $\eta=5.7$ degrees. $R_N$ is reduced by reducing aperture diameter or fluid velocity.

A major limiting factor in the sensitivity of the ESZ instruments is that the threshold voltage 42 must be almost always above the peak of the noise voltage at the output of the pulse amplifier 36. For this to happen, the threshold voltage 42 must be up to eight times the r.m.s. noise voltage. Such a high threshold voltage 42 means that no signals are detectable unless the signal pulse peaks are much higher than the r.m.s. noise level.

To detect particles 22 that would produce pulse peaks at the output of the pulse amplifier 36 below the threshold voltage 42, many particles 22 must be passed simultaneously through the aperture 18. To accurately detect the concentrated particles 22, the pulse shapes produced must be uniform. To obtain uniform pulse shapes, Golibersuch used a long, narrow, circular, cylindrical, aperture 18a. Uniform pulse shapes can be obtained, with better results, if either a double-tapered aperture 18b or a single-tapered aperture 18c is used. The diameter 54a, 54b could be in the range of 30 μm to 100 μm, but may have other sizes. The object of using an aperture 18b, 18c with concentrated particles 22 is to measure the lower-order statistical moments of the particle 22 size distribution to calculate a particle 22 size distribution obtained by single-particle 22 measurement below the threshold voltage 42.

The fundamental formula I used for determining the moments of the particle size distribution using concentrated particles 22 in the aperture 18b, 18c is $$\lambda_n = <A^n> \int_{-\infty}^{\infty} f^n(t)dt \qquad \text{(Eqn 1)}.$$

Figure 3:
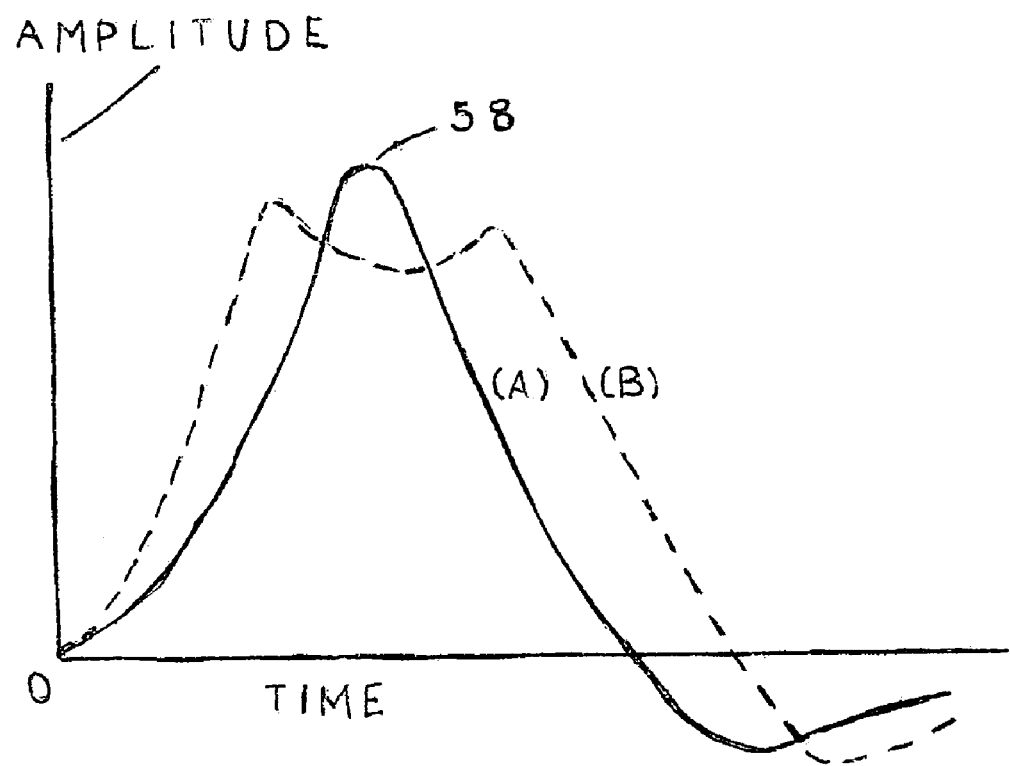
FIG. 3 shows in solid line a typical signal pulse of a particle coaxially traveling through the aperture of an ESZ instrument, such as the one represented in FIG. 1. The dashed line curve represents a particle that does not travel coaxially through the aperture.
Figure 6:
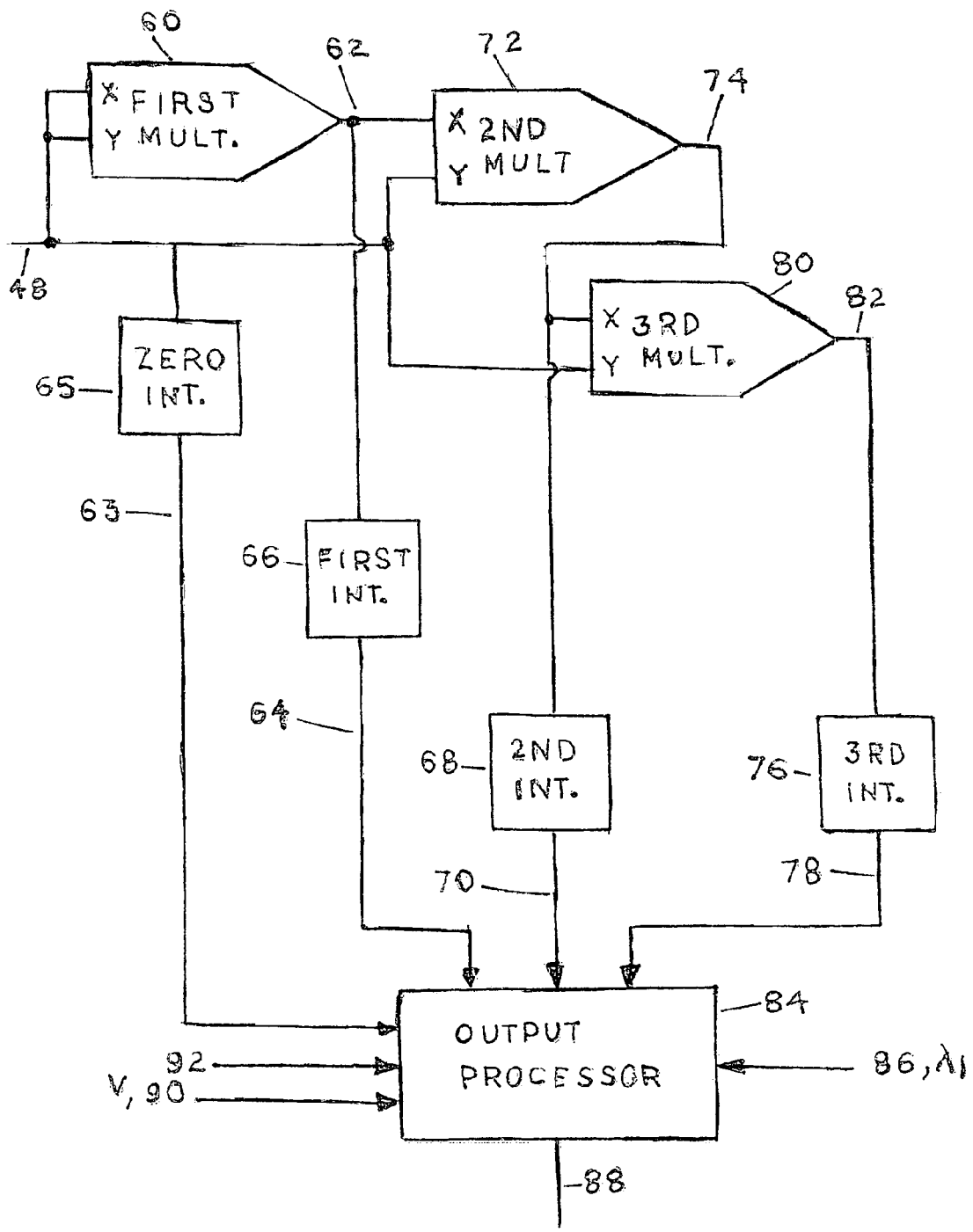
FIG. 6 is a schematic representation of a signal processor circuit to compute the lower-order statistical moments of the particle size distribution for one of the preferred embodiments.

$\lambda_n$ is measured by the system of FIG. 6, and is related to the $n^{th}$ statistical moment of the particle size distribution. f(t) is the signal pulse of FIG. 3a. This pulse has nearly the same shape, regardless of the size or shape of the particle 22. A is the pulse peak 5S, which is proportional to the particle 22 volume. v is the number of particles 22 passing through the aperture 18b, 18c per second; so v must be found by some external instrument with more sensitivity for particle counting. Some assumption can be made that eliminates the need to measure v directly.

The input of the system of FIG. 6 comes from the output of the pulse amplifier 36, which is 48. To find $\lambda_1$, the D.C. coupling voltage 33 is used in place of the D.C. voltage blocking capacitor 32. To find $\lambda_n$ for n>1, the D.C. voltage blocking capacitor 32 will be used in place of the D.C. coupling voltage 33. $\lambda_1$ provides information about the first statistical moment (mean) of the particle size distribution, and is the output 63 of the zeroth integrator 65, which gives the integral of the pulse amplifier output 48. It is possible to obtain the information provided by $\lambda_1$ without using the zeroth integrator 65, by finding the volumetric concentration of particles 22 in the electrolyte 21, and finding the volumetric flow rate of the electrolytic solution 21 through the aperture 18b, 18c. This gives the volumetric flow rate of particles 22 through the aperture 18b, 18c. Eliminating the zeroth integrator 65 eliminates the need for D.C. coupling voltage 33. It is desirable to use only A.C. coupling in an ESZ instrument because low frequency noise and drift are eliminated. $\lambda_2$ provides information about the second statistical moment (variance) about zero of the particle size distribution, and is the output 64 of the first integrator 66, which gives the integral of the square of the pulse amplifier output 48. The squaring function is provided by first multiplier 60. The first multiplier output 62 is connected to the input of the first integrator 66.

If $\lambda_1$ and $\lambda_2$ are measured, v<A> and v<$A^2$>can be found because the pulse shape f(t) is known, and the integrals of Eqn 1 involving f(t) and $f^2(t)$ can be calculated. To find the mean and variance, it is necessary to find v. v is closely related to the particle 22 number density in the electrolytic solution 21. If the particles 22 are very small, an ultramicroscope, or a similar instrument, would be needed to find the particle 22 number density. If the sample does not have particles less than about 30 nanometers (nm) in diameter, a conventional dark-field microscope is sensitive enough to detect the particles.

A kind of ultramicroscope that would eliminate the tedium of visually counting particles is called the "flow ultramicroscope." It is an automated instrument that counts particles by detecting them as they scatter light to a photodetector while passing through an intense light beam. Light scattering does not give an accurate indication of particle size, but it can be very sensitive to the presence of a particle. Such devices are commercially available for counting particles in samples of ultrapure liquids. They can be adapted for particle number density measurements in a liquid.

$\lambda_3$ provides information about the third statistical moment (skew) about zero of the particle size distribution, and is the output 70 of the second integrator 68, which provides the integral of the cube of the pulse amplifier output 48. The cubing function is provided by the first multiplier 60 and the second multiplier 72. The second multiplier output 74 is connected to the second integrator 68 input.

One way to extrapolate a particle size distribution is to assume the form of the distribution. Several kinds of distributions have been assumed in particle size analysis, but the one that has more physical justification than others is the log normal distribution. Many materials approximate a log normal distribution.

$\lambda_4$ provides information about the fourth statistical moment (kurtosis) about zero of the particle size distribution, and is the output 78 of the third integrator 76, which provides the integral of the fourth power of the pulse amplifier output 48. The fourth power function is provided by the first multiplier 60, the second multiplier 72, and the third multiplier 80. The third multiplier output 82 is connected to the third integrator 76 input.

FIG. 6 does not show how to obtain $\lambda_5$, but it is obvious from examining FIG. 6 how to obtain any value of $\lambda_n$.

The integral of the signal is proportional to the mean of the particle size distribution curve. The integral of the square of the signal is related to the variance of the particle size distribution curve. The integral of the third power of the signal is related to the skew of the particle size distribution curve. The integral of the fourth power of the signal is related to the kurtosis or peakedness of the particle size distribution curve.

Higher powers of the signal do not have specific names but are also relevant. They are more difficult to compute. For the purposes of the present invention, however, it has been found that computing these first four statistical moments, namely, the mean, the variance, the skew and kurtosis of the particle size distribution curve, provides the necessary information to accurately estimate the shape of the particle distribution.

The integrator outputs 63, 64, 70, and 78 are applied to an output processor 84 that gives a particle size distribution estimate 88. If $\lambda_1$ is not obtained from the zeroth integrator output 63, it is applied to the output processor 84 at $\lambda_1$ input 86. If v is not calculated by assuming the form of the particle size distribution, it is applied to the output processor 84 at v input 90.

It is possible to find the parameters of a log normal distribution by only knowing $\lambda_1$ and the particle size distribution above the threshold voltage 42 obtained by using the ESZ instrument for single-particle 22 measurement. From $\lambda_1$ one can calculate the total volume of the sample. From the particle size distribution above the volume representing the threshold voltage 42, combined with the total volume of the sample, we can compute the cumulative particle size distribution.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An electrical sensing zone apparatus having an aperture with tapered outlet and an inlet of a predetermined diameter and said aperture having a length of at least 30 micrometers, said aperture being immersed in an electrolyte solution with particles of at least one size, said solution being caused to pass through said aperture, and the improvement comprising means for causing said solution to pass through said aperture at selectable liquid flow rate with Reynolds number between 1 and 10 to preclude boundary layer separation effects inside and adjacent to said aperture wherein said aperture has a single-tapered shape that approximates one half of a hyperboloid of one sheet and said single-tapered shape has an angle between 74.5 degrees and 45.8 degrees.

2. A method for counting and measuring particles suspended in an electrolytic solution, comprising the steps of passing said solution through an electrical sensing zone device including an aperture at a selectable flow rate with Reynolds number between 1 and 10 to preclude boundary layer separation effects inside and adjacent to said aperture wherein said aperture has a single-tapered shape that approximates one half of a hyperboloid of one sheet and said single-tapered shape has all angle between 74.5 degrees and 45.8 degrees.

3. An electrical sensing zone apparatus having an aperture with tapered outlet and an inlet of a predetermined diameter and said aperture having a length of at least 30 micrometers, said aperture being immersed in an electrolyte solution with particles of at least one size, said solution being caused to pass through said aperture, and the improvement comprising means for causing said solution to pass through said aperture at selectable liquid flow rate with Reynolds number between 1 and 10 to preclude boundary layer separation effects inside and adjacent to said aperture wherein said aperture has a double-tapered shape that approximates one half of a hyperboloid of one sheet and said double-tapered shape has an angle between 74.5 degrees and 45.8 degrees.

4. A method for counting and measuring particles suspended in an electrolytic solution, comprising the steps of passing said solution through an electrical sensing zone device including an aperture at a selectable flow rate with Reynolds number between 1 and 10 to preclude boundary layer separation effects inside and adjacent to said aperture wherein said aperture has a double-tapered share that approximates one half of a hyperboloid of one sheet and said double-tapered shape has an angle between 74.5 degrees and 45.8 degrees.

* * * * *